US007275930B2

(12) United States Patent
Taub et al.

(10) Patent No.: US 7,275,930 B2
(45) Date of Patent: *Oct. 2, 2007

(54) VIRTUAL ORTHODONTIC TREATMENT

(75) Inventors: Eldad Taub, Reut (IL); Avi Kopelman, Ramat-Chen (IL)

(73) Assignee: Cadent Ltd, OR Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/749,388

(22) Filed: Jan. 2, 2004

(65) Prior Publication Data
US 2004/0142298 A1     Jul. 22, 2004

Related U.S. Application Data

(63) Continuation of application No. 09/591,757, filed on Jun. 12, 2000, now Pat. No. 6,739,869, which is a continuation of application No. PCT/IL98/00593, filed on Dec. 7, 1998.

(30) Foreign Application Priority Data
Dec. 30, 1997   (IL)   ..................... 122807

(51) Int. Cl.
*A61C 3/00*     (2006.01)
(52) U.S. Cl. ....................... 433/24; 433/213
(58) Field of Classification Search ............... 433/24, 433/213
See application file for complete search history.

(56) References Cited

U.S. PATENT DOCUMENTS 5,338,198 A * 8/1994 Wu et al. .................. 433/213

| 5,464,349 | A | 11/1995 | Andreiko et al. ............. 433/24 |
| RE35,169 | E | 3/1996 | Lemchen et al. ............. 433/24 |
| 5,533,895 | A | 7/1996 | Andreiko et al. ............. 433/24 |
| 5,879,158 | A | 3/1999 | Doyle et al. .................. 433/24 |
| 6,334,853 | B1 | 1/2002 | Kopelman et al. |
| 6,350,120 | B1 * | 2/2002 | Sachdeva et al. ............. 433/24 |
| 6,471,511 | B1 * | 10/2002 | Chishti et al. ................ 433/24 |
| 6,739,869 | B1 | 5/2004 | Taub et al. |

FOREIGN PATENT DOCUMENTS

| JP | 5-168654 | 7/1993 |
| JP | 5-261124 | 10/1993 |

(Continued)

OTHER PUBLICATIONS

Computer Treatment Estimates in Orthodontics and Orthognathic Surgery, Journal of Clinical Orthodontics, Guess et al., Volumn 1989, Apr. (262-268), 1997.*

(Continued)

*Primary Examiner*—John J Wilson
(74) *Attorney, Agent, or Firm*—The Nath Law Group; Jerald L. Meyer; Derek Richmond

(57) ABSTRACT

A method for virtual orthodontic treatment is provided in which a virtual set of orthodontic components is associated, in a virtual space, with a first virtual three-dimensional image of teeth, and then by a set of rules which define the effect of the set of components' teeth, the effect of the virtual treatment can be computed. This virtual treatment can be used to predict the results of a real-life orthodontic treatment as to design such a treatment.

28 Claims, 9 Drawing Sheets

FOREIGN PATENT DOCUMENTS

| | | |
|---|---|---|
| JP | 7-222759 | 8/1995 |
| JP | 8-168499 | 7/1996 |
| JP | 8-280715 | 10/1996 |
| WO | WO94/10935 | 5/1994 |
| WO | WO97/03622 | 2/1997 |
| WO | WO 01/80761 | 11/2001 |

OTHER PUBLICATIONS

Guess, M.B. et al., "Computer treatment Estimates in Orthodonticvs and Orthognathic Surgery", *JCO on CD-ROM*, pp. 1-11, vol. 1989 Apr. (262-268), 1997.

* cited by examiner

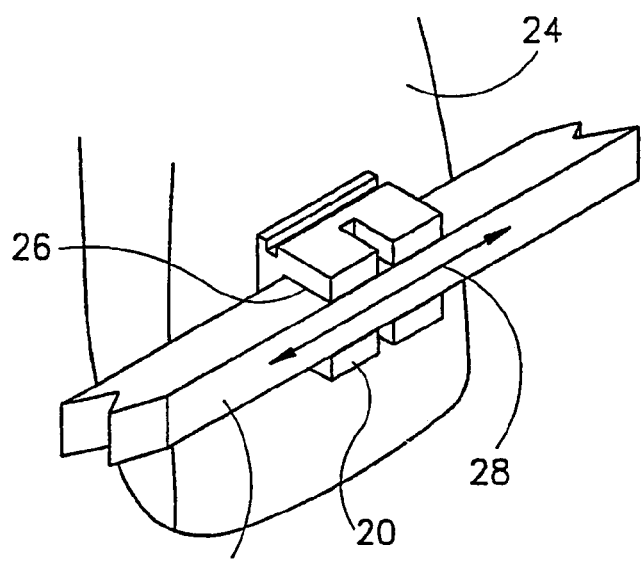
FIG.1
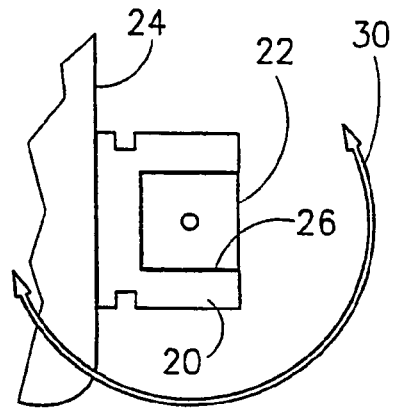
FIG.2
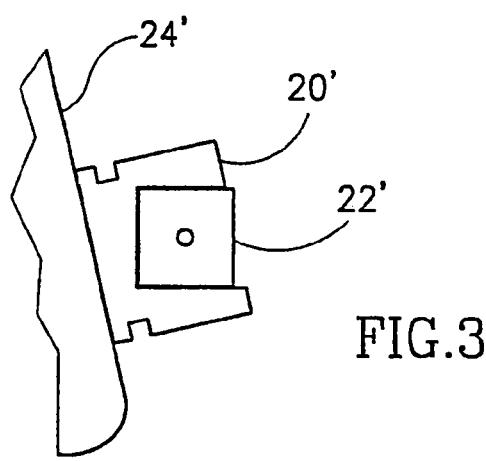
FIG.3
| BAND | BRACKET | WIRE | VECTOR |
|------|---------|------|--------|
| TOOTH | | | |
UR ☐ ☐ ☐ ☐ ☐   ☐ ☐ ☐ ☐ ☐ UL
    5 4 3 2 1   1 2 3 4 5
LR ☐ ☐ ☐ ☐ ☐   ☐ ☐ ☐ ☐ ☐ LL
Open
FIG.4

VIRTUAL ORTHODONTIC TREATMENT

This is a Continuation application of U.S. patent application Ser. No. 09/591,757 filed Jun. 12, 2000 now U.S. Pat. No. 6,739,869 which is a Continuation of PCT/IL98/00593 filed Dec. 7, 1998 which claims priority to Israel patent application no. 122807 filed Dec. 30, 1997, the entire contents of which are hereby incorporated by reference in its entirety.

FIELD AND BACKGROUND OF THE INVENTION

The present invention is generally in the field of orthodontics.

An orthodontic treatment has the objects of moving and reorienting teeth for both functional or aesthetic purposes. In such a treatment, the orthodont places a variety of orthodontic components on the teeth including brackets, which are firmly fixed to the teeth, and other components including wires, tensioning springs, etc., which apply forces and moments on the teeth, through the brackets, thereby causing the teeth to move. A major problem facing the orthodont is to predict the final outcome of the orthodontic treatment. Another problem to focus is to define the proper placement of the brackets and to select the proper force-inducing components to best yield the desired-outcome. Currently, the design and predicting of orthodontic treatment is based mainly on the orthodont's personal "look and feel" and prior experience skills. This approach is not only error prone but also varies from one individual to the other, which is obviously undesired.

There is accordingly a need in the art to provide the orthodont with a tool for visual demonstration, design or predicting of possible outcome of an orthodontic treatment. Provided by the invention are method and system therefor.

GENERAL DESCRIPTION OF THE INVENTION

In the context of the present description and the appended claims, the term "movement" or "moving" refers to repositioning teeth, reorientating teeth, or both. The term "orthodontic treatment" refers to a treatment intended to move at least one tooth; namely, an orthodontic treatment should be understood as encompassing a procedure where all or only part of the teeth (e.g. teeth of one jaw, a group of teeth in a section of a jaw, etc.) are moved. Furthermore, the term "orthodontic treatment" refers both to a treatment intended to yield movement to reach a final, close to ideal outcome of the treatment as well as to an interim treatment yielding an interim position and orientation of the teeth. In other words, the term "orthodontic treatment" mentioned herein encompasses both a treatment from an initial stage, i.e. before the treatment began, through to a final stage; a treatment from an initial stage to an interim stage; as well as to a treatment from an interim stage to another interim or final stage.

The term "virtual treatment" (referred to also, occasionally as virtual orthodontic treatment) as used herein means an orthodontic treatment as simulated on a computer. A vital treatment may use virtual components (i.e. 'component' in the virtu computer environment) such as brackets, wires, tensioning springs or lubber bands, corresponding to real components as used in a real life orthodontic treatment, but may also use components which are not normally used in real-life treatment; and also components used in real-life treatment but are used in the virtual treatment in a different manner. Thus, for example, a virtual orthodontic treatment may use wires which are not normally used in a real life orthodontic treatment; may use wires of a cross-section other than such used in a real-life orthodontic treatment; may combine wires and brackets in a manner whereby the brackets are biased towards a rotational movement around the axis of the wire which is usually not performed in a real-life orthodontic treatment; etc. It will therefore be understood that the result of virtual treatment is not necessarily the same as the actual real treatment.

In the following, a method and system for virtual treatment is disclosed. Manual systems may be used by an orthodont to examine various alternative treatment paradigms and compare them to one another so as to see which one will yield the best result. For example, the orthodont may compare a treatment where one or more teeth are extracted to another treatment where all teeth are left in tact. In addition, the system and method of the invention may allow also the orthodont to select the orthodontic components which he will eventually use in the real-life treatment, to predict the course, time and cost of the treatment. This will all be clarified from the disclosure below.

It will also become clear from the following disclosure, the orthodontic treatment may be made to resemble a real-life orthodontic treatment, although not necessarily so, and occasionally, the orthodontic treatment may use components or may apply a set of rules which are not directly applicable to real-life treatment.

The present invention provides, by one of its aspects, a method for virtual orthodontic treatment, comprising:

(a) providing a first virtual three-dimensional image indicative of a three-dimensional (3D) model of teeth from at least one jaw, the model being manipulable so as to allow its viewing from a desired direction;

(b) selecting a virtual set of orthodontic components, and associating the components with the teeth of said first image so as to obtain a second image of said 3D model with said components associated therewith;

(c) using a set of rules, including at least one rule, defining the effect of said set of components on said teeth, computing the manner of movement of the teeth as a result of said effect, so as to obtain a third image comprising the teeth model following the virtual treatment.

The set of orthodontic components selected in step (b) includes components which are capable of imparting movement between at least two teeth. For example, the set may include at least two brackets and a wire, may include rubber bands or tensioning springs for forcing two teeth one against the other, etc. Typically, the set of orthodontic components includes for each jaw, typically, but not necessarily, about 5 to about 10 brackets in the case of a child's jaw, and between about 5 to about 16 in the case of an adult's jaw.

The set of orthodontic components may be represented as an image which is similar to the image of the real orthodontic component, as seen in real life. However, orthodontic component may also be represented by any other graphic representations. For example, the wire may be represented by a straight or curved line; a bracket may be represented by a rectangular frame, etc.

In accordance with some embodiments of the invention, the set of components includes brackets and a wire and the rule dictates that eventually all slots which receive the wire will be aligned with the wire where the latter is arranged as a splined curve indicative of the desired result of the virtual treatment. In other words, in this case the wire represents the desired results of alignment of all slots following the virtual treatment. Thus, by such an embodiment a component which represents a real-life component, i.e. a wire, is used in a different manner than in a real-life treatment in that it dictates the result of the treatment. This embodiment thus illustrates a general principle in some embodiments of the invention that while in a real-life treatment components act in combination to apply forces on teeth and the movement is a result of such applied forces, in a virtual treatment of the invention, the components may also dictate the final result. However, this does not exclude a possibility, in accordance with some other embodiments of the invention, where the movement of the teeth is dictated by forces and moments, which in this case are the set of rules, which act on the teeth under influence of the different components.

Thus, as will be appreciated, occasionally, the component and the set of rules may be associated with one another. Taking the previously illustrated embodiment as an example, the component, which is a wire defining a splined curve, has with it an associated rule dictating that the brackets, with the associated teeth, should move, vertically, but possibly also horizontally, so that all brackets will eventually be positioned such that their respective slots are on the splined curve defined by the wire. In addition to the desired final result, the set of rules may also stipulate the computational algorithm defining the manner of movement of the teeth to yield said final result.

The set of rules may also allow, for example, the removal of the tooth in certain circumstances. For example, in the case of crowdness, i.e. insufficient space for all teeth to assume an ideal position and orientation (a position and orientation such that the apex of all teeth are essentially on one splined curve), an interfering tooth may be removed. The removal may, by one embodiment, be automatic; by another embodiment, the user may decide in such a case which tooth is to be removed.

As will be explained in greater detail below, the set of rules is not limited to a specific implementation. Thus, by way of example, the set of rules may be extracted from a static set of rule database, or by way of another example from a dynamic learning database holding a rule base that may be adjusted depending upon e.g. various characteristics of the individual patient that undergoes the treatment.

The purpose of the virtual orthodontic treatment may be to change the relative orientation of the teeth, to change a distance between the teeth, to alter the inter-occlusion of distance between teeth of opposite jaws, etc.

In accordance with one example, where the teeth are such that they do not fill the entire space in a jaw (namely with an edge of one tooth being in proximity to a neighbouring tooth), the set of rules may also allow the addition of a tooth, which may, in the case of a child's jaw, represent a tooth which has not yet grown or, in the case of an adult's jaw, a crown which may be implanted in a real-life treatment.

Steps (b) and (c) may be repeated a plurality of times until obtaining a desired result of the virtual treatment. In a reseated step (b), a component already selected in a previous step may associated with the teeth model in a different manner, e.g. applying it on a different tooth, orienting it on a tooth in a different manner, etc.; or new components may be selected, e.g. new brackets, new rubber bands, a different wire; etc.

The 3D teeth model may be of all teeth in a jaw, may be a model of teeth of both jaws, may be a model of part of the teeth of one or both jaws.

The term "associating" as used herein denotes the entire range of combining orthodontic components with teeth and to typically (but not necessarily) in a manner that stimulates combination thereof in real life treatment. Typical, but not exclusive examples, being: attaching brackets to teeth at different positions or orientations; fixing a wire into the bracket's wire-receiving slot; sliding the bracket and the wire one with respect to another, changing the angle of the wire-receiving slot within the bracket so as to change the torque or moment between the wire and the bracket; fixing a tensioning spring or band around two adjacent teeth; etc. The wire chosen within the framework of the virtual treatment may have various geometries, e.g. straight or spline curved, and various cross-sectional shapes, e.g. circular, oval, rectangular, etc. (usually to track the ideal curvature of the teeth arrangement in a jaw).

In accordance with another aspect of the invention; there is provided a method for designing orthodontic treatment of teeth from at least one jaw, comprising:

(a) providing a virtual three-dimensional image indicative of a three-dimensional model of the teeth in a manner allowing manipulation of the model for viewing the model from a desired direction;

(b) selecting a virtual set of orthodontic components corresponding to those intended to be used in said orthodontic treatment and associating the components with the teeth of said first image so as to obtain a second image of said three-dimensional model with said components associated therewith in a manner representing the manner in which said components and the teeth may be combined in said orthodontic treatment;

(c) using a set of rules, including at least one rule, defining the manner in which said components affect movement of the teeth, so as to obtain a third image comprising the teeth model after movement of the teeth affected by said components;

(d) repeating steps (a) and (c) until a desired third image is obtained, which desired third image represents a desired position and orientation of teeth following the orthodontic treatment;

(e) recording said second image which yields, following step (c), the desired third image and using it as a basis for designing the orthodontic treatment.

In addition to allowing a design of the treatment, the method in accordance with the second aspect may also be used to predict the length of the treatment as well as its costs.

By a further aspect the present invention provides a system for a virtual orthodontic treatment, comprising:

(a) storage means capable of storing a first virtual three-dimensional image indicative of a three-dimensional model of teeth of at least one, substantially entire jaw;

(b) user interface for enabling selection of a virtual set of orthodontic components;

(c) processor capable of at least:

(c1) manipulating said three-dimensional model to allow its viewing from a desired direction, (c2) associating said set with the teeth of said first image to obtain a third image of said three-dimensional model with said components associated therewith, and (c3) applying a set of rules, including at least one rule, determining effect of said components on the teeth so as to cause virtual movement of the teeth as a result of association with said components to obtain a third teeth model; and (d) display means for displaying the images.

Regardless of the aspect under consideration, the generation of virtual three-dimensional image may be obtained, e.g by following the technique described in PCT Publication No. WO 97/03622, the contents of which is incorporated herein by reference.

By a still further aspect the present invention provides an apparatus having a memory which contains a digital image representing a three-dimensional teeth model following a virtual orthodontic treatment, which image was generated by any of the above methods.

By a further aspect there is provided a memory for storing data for access by an application program, implementing the steps (b)-(c) according to a method of each of the above aspects; the application program being executed on a data processing system; the data representing a first virtual three-dimensional image, indicative of the three-dimensional model of teeth of one jaw. Also provided is a memory for storing data representing a second virtual three-dimensional image, obtained by implementing the above method.

BRIEF DESCRIPTION OF THE DRAWINGS

For a better understanding, the invention will now be described by way of example only with reference to the annexed drawings in which:

FIG. 1 illustrates two components, a bracket and a wire, selectable by the user in a virtual treatment in accordance with one embodiment of the invention;

FIG. 2 is a cross-sectional view along line I-I in FIG. 2;

FIG. 3 is the same cross-sectional view as in FIG. 2, after change in the slot angle;

FIG. 4 illustrates one view of user interface, according to an embodiment of the invention;

FIG. 6B and FIG. 6C illustrate the manner in which the wire is viewed in various steps of the process of FIG. 6a;

DETAILED DESCRIPTION OF THE INVENTION

Figure 5A:
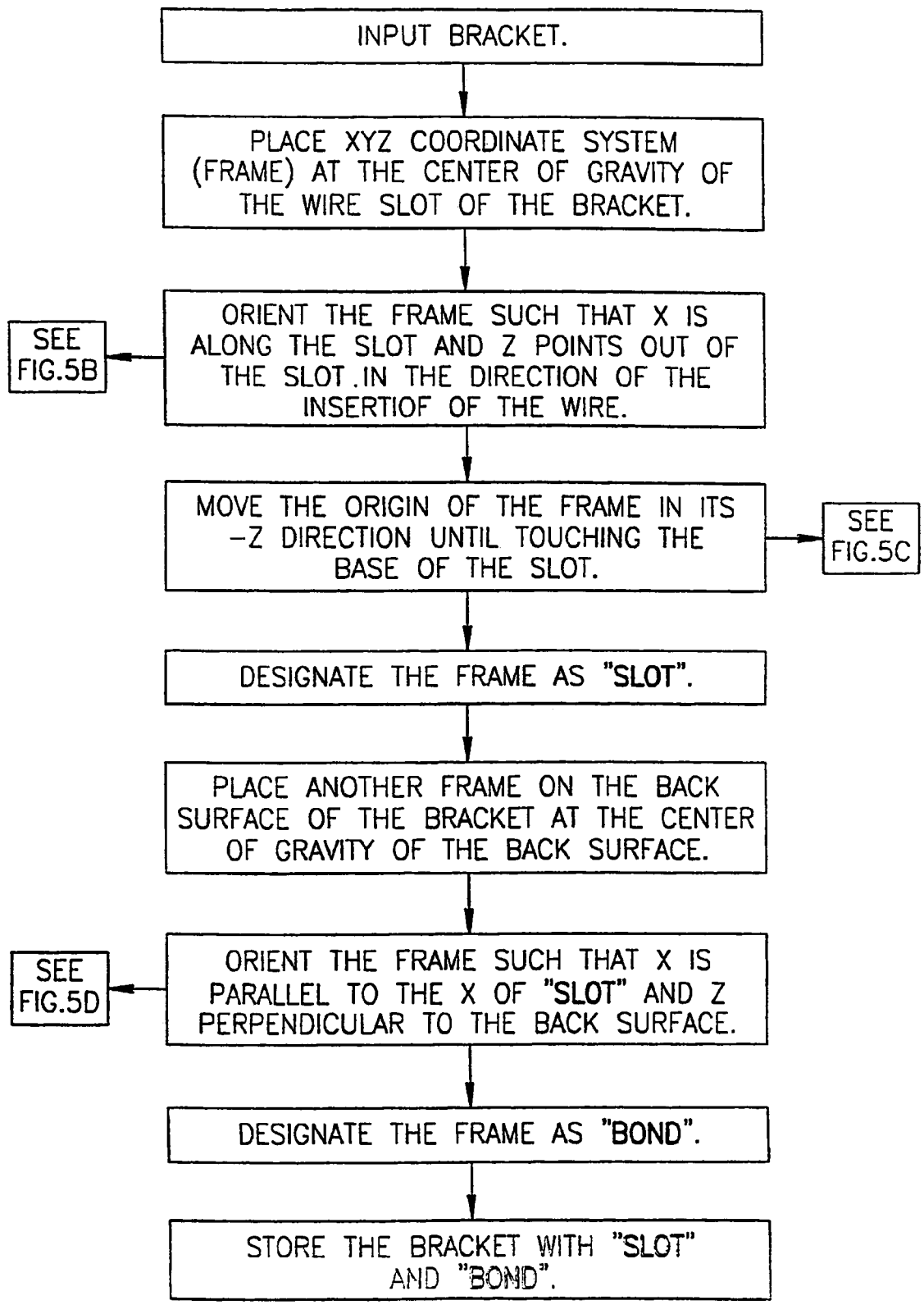
FIG. 5A is a block diagram illustrating the manner of defining a brackets for use in the framework of virtual treatment in accordance with an embodiment of the invention.

The present invention provides a method and system for virtual movement of teeth using the framework or a set of rules from which is based in real life, although not necessarily identical.

In the following, the invention may at times be described with a reference made to various physical entities, such as "jaw", "bracket", "wire", "band", etc. It should, however, be understood that it implies, in most cases, to a representation of these entities that is used in the virtual treatment. There are some exceptions where reference is made to real physical objects, which fact may clearly be inferred based on the context.

Teeth movement in a virtual, computerized 3D environment for the purpose of planning an orthodontic treatment or for any other purpose, is a complicated task if this is being performed using hitherto known techniques. The use of techniques known to the orthodont from a real orthodontic treatment, simplifies this virtual orthodontic treatment.

The virtual treatment may be required, at ties, to allow the orthodont to determine a potential outcome of orthodontic treatment. For such a purpose, the virtual treatment need not necessarily follow a course to be followed by the real orthodontic treatment since the focus may be only on the final outcome, namely on the final position and orientation of the teeth following the treatment. In such a treatment, the orthodont may utilize orthodontic components and combination between such components, even such not used in real life orthodontic treatment. Examples are a selection of a wire with a different geometry than that used in real life or, change in the slot angle within the brackets so as to yield an angular moment on the teeth about the axis of the wire (see FIG. 3).

If, however, a virtual treatment is intended to simulate the real treatment for the purpose of treatment design, preferably (but not necessarily), only orthodontic components which simulate those used in real life orthodontic treatment, will be used.

In a typical yet not exclusive sequence of operation in virtual treatment, the user first selects brackets and places them at appropriate positions on the surface of selected teeth, usually all teeth of the jaws. In most cases brackets are placed on the buckal teeth surface; however, occasionally, in the virtual treatment brackets may alternatively or additionally be placed on lingual surfaces of the teeth (this may also be followed at times in real life orthodontic treatment).

At a next step, the user may define the final desired distance between the teeth (the default is usually zero) and then selects an arch-wire from a library of such wires. The library may include wires of different widths, different cross-sectional shapes, and different geometries. Optionally, it is possible also to change the geometry of the selected wire, e.g to make it to follow a tortous path in a vertical and/or a horizontal plane, etc.

Thereafter, the wire may be associated with the teeth model, for example, by combining them with virtual brackets fitted on the teeth surface or by attaching them first to virtual anchoring molars, and then to virtual brackets, etc. The effect of the components on each tooth is thereafter computed by the system, based on the set of rules to determine the outcome of the virtual treatment.

If the virtual treatment uses components which simulate real-life components, once an optimal result of virtual treatment is reached, the parameters, namely the type of components which were used and the manner they were combined with one another and with the teeth model, may be recorded and this may then used to generate a prescription for the orthodontic treatment. Such a prescription may specific the type of components used, the exact position of each component, e.g. the position of the bracket on each tooth, etc.

The virtual treatment may obviously also provide a tool to estimate the treatment length and costs.

The invention will now be further illustrated with reference to some specific, non-limiting embodiments, with reference to the annexed drawings.

FIGS. 1-3 show examples of a set of components which can be used in accordance with an embodiment of the invention. In this specific embodiment, the components consist of a bracket 20 and wire 22 fixed on a surface of a tooth 24, of which only a portion thereof represented by a rectangle is seen. The user has freedom of choice of the exact position of attachment of the bracket 20 on the surface of the tooth 24 and also can slide wire 20 in a longitudinal axis within the receiving slot 26 of the bracket, as represented by the bi-directional arrow 28.

The wire and the bracket may be associated with one another in different relative orientations. In the example shown in FIGS. 1 and 2, the wire, which in this case has a rectangular cross-section, is received in a slot with walls parallel and normal to the tooth's surface. By some embodiments of the invention it is possible to change the angle of slot 26 about its central axis, as represented by arrow 30, in FIG. 2 to yield a state such as that shown in FIG. 3, wherein wire 22' has a different angular orientation, with respect to bracket 20', thereby applying a moment onto tooth 24'.

FIG. 4 shows an example of an embodiment of one out of many possible variants of a user interface for realizing the initial component selection steps. The user can select the brackets from a library of brackets, and similarly can select wires, bands etc. from corresponding libraries. In addition, the user has the ability to determine the type of forces and their direction which will act on each tooth.

Figure 5B:
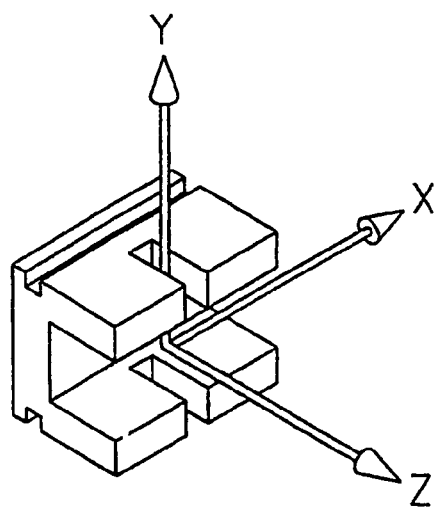
FIGS. 5B-5D illustrate the brackets as viewed in various steps of the selection process.
Figure 5C:
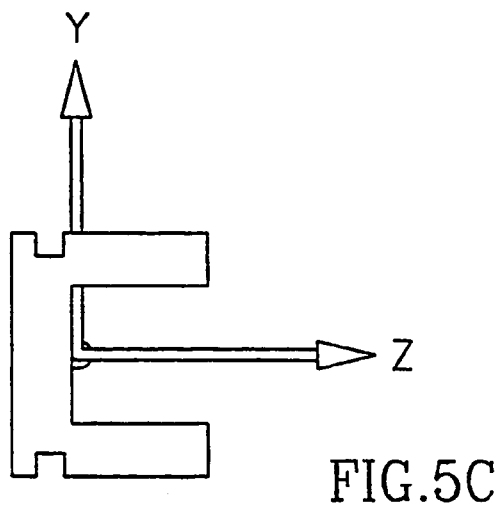
Figure 5D:
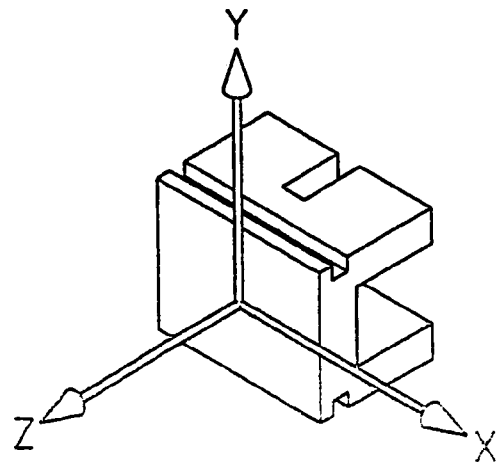

FIG. 5A illustrates the manner of defining a bracket for use in subsequent virtual treatment steps. In this process, the bracket is defined with respect to a relative; coordinate system to allow its subsequent association with the wire, thus defining a "SLOT" frame of reference; (illustrated graphically in FIGS. 5B and 5C) as well as to define another coordinate system to facilitate attachment of the bracket to the teeth, thus defining the "BOND" reference frame (illustrated graphically in FIG. 5D).

Although the steps of bracket definition are typically carried once, while creating the bracket library, it may also be repeated prior to each virtual treatment step while selecting brackets for the treatment.

Figure 6A:
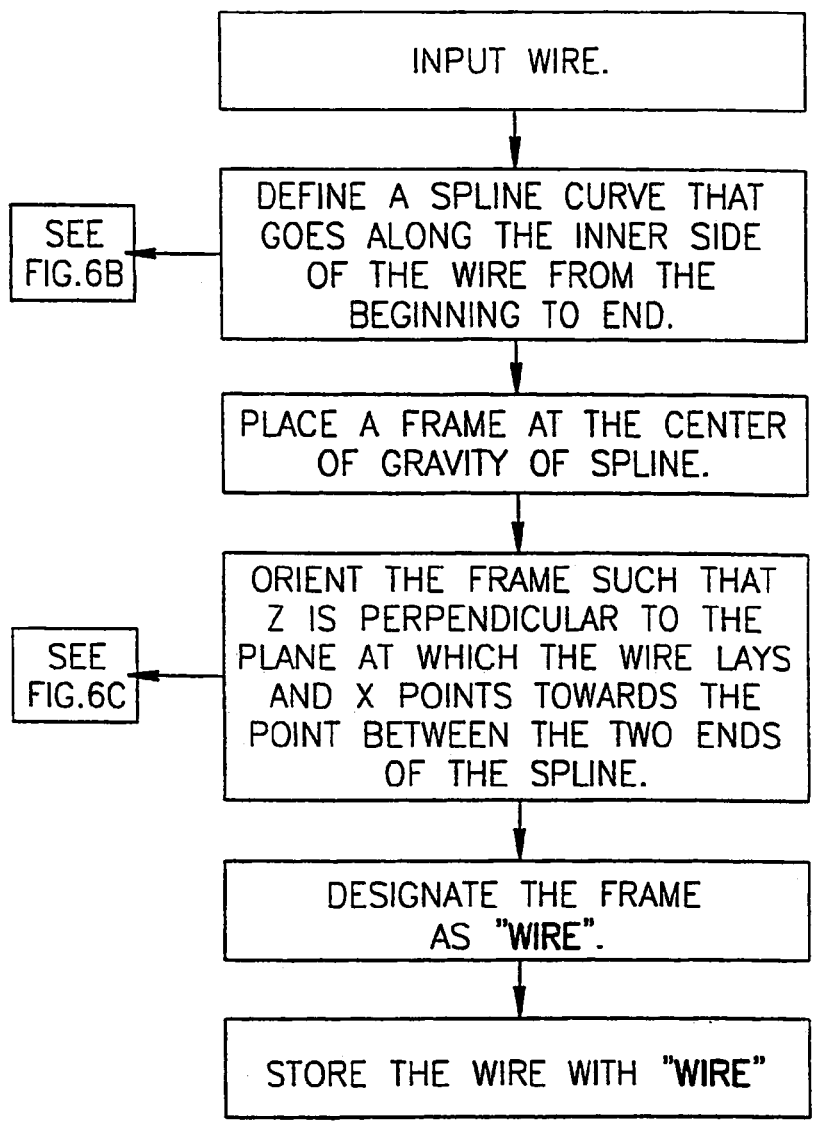
FIG. 6A is a block diagram illustrating the manner of defining a wire for use within the framework of a virtual treatment in accordance with an embodiment of the invention.
Figures 6B, 6C:
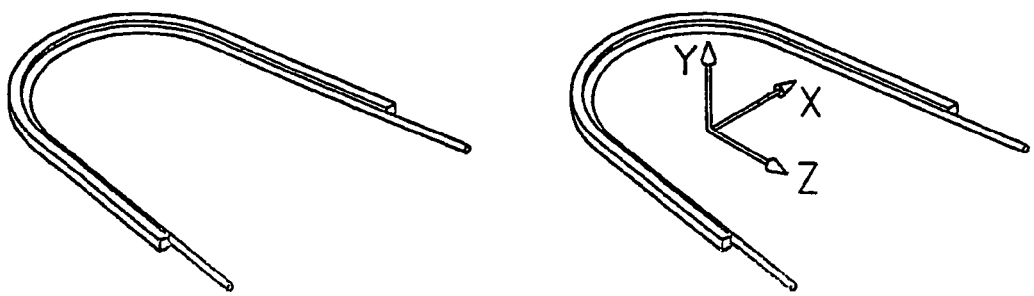

FIG. 6A illustrates the steps of choosing a wire and defining it such that it can be subsequently used in the framework of virtual treatment. A wire is selected, its initial curve is defined (illustrated graphically in FIG. 6B) and then the wire is placed in a relative coordinate system (illustrated graphically in FIG. 6C), so as to define a "WIRE" frame of reference, for subsequent use. Obviously, as will be appreciated, the x-y-z coordinate system of the "WIRE" frame of reference should correspond to the x-y-z coordinate system of the "SLOT" reference frame.

Figure 7:
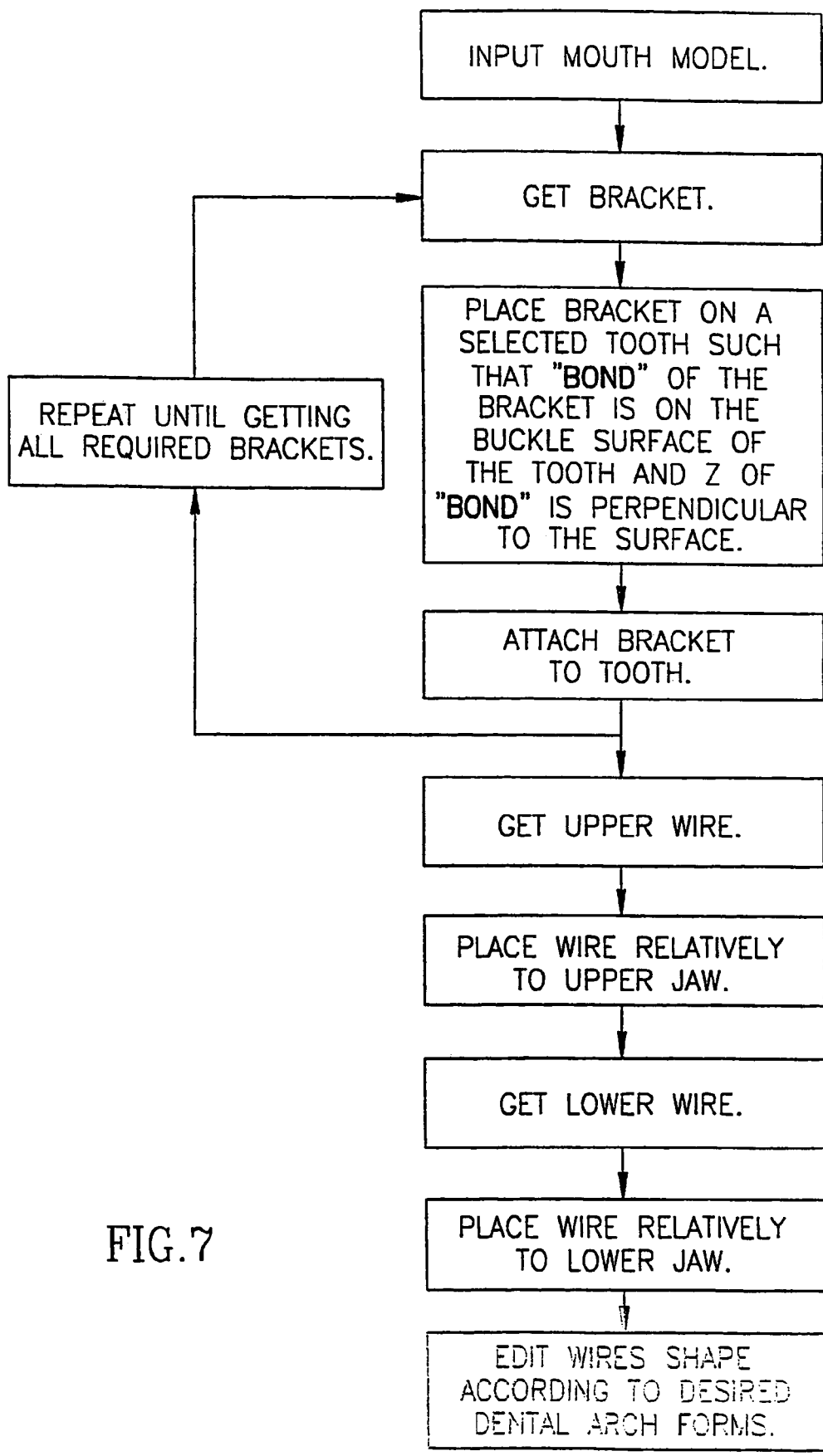
FIG. 7 is a block diagram illustrating the manner of attaching the brackets onto teeth in the virtual treatment, in accordance with an embodiment of the invention.

FIG. 7 illustrates the steps of attachment of a bracket onto a tooth. A teeth model is acquired, brackets are selected from the library and each bracket is placed on a tooth using the "BOND" reference frame, such that the z axis of the BOND frame of reference is perpendicular to the surface. Once the bracket is placed at the desired location, it is both fixed in this location and then the process is repeated a plurality of times in accordance with the number of brackets to be placed on the teeth.

Figure 8:
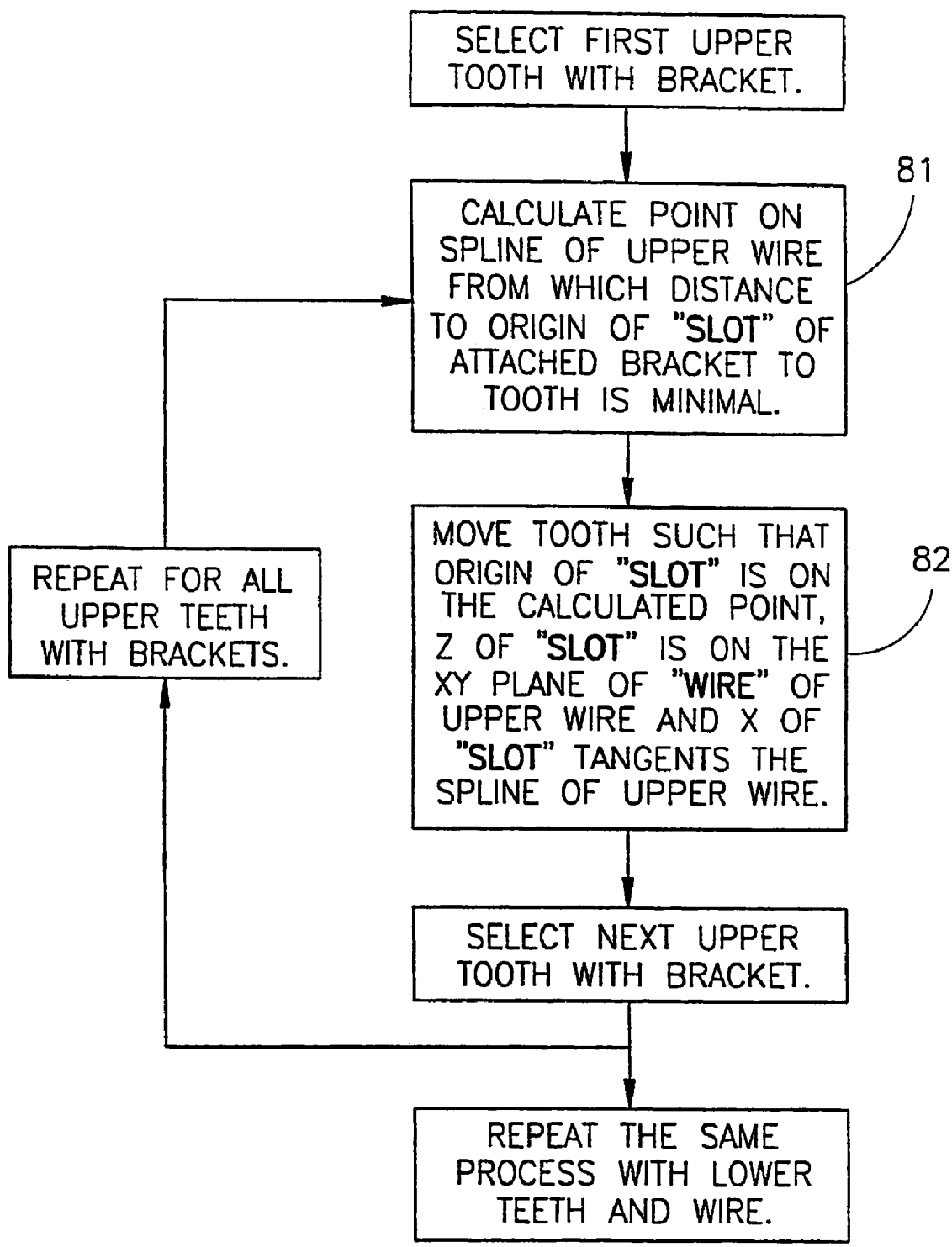
FIG. 8 is a block diagram illustrating the steps of matching wires to jaws and vertical movement of teeth to a position dictated by the wire.

FIG. 8 illustrates the steps of matching the wires to the jaws. The wires are selected from a library, and placed so that their spline curve will match that of the jaw or their spline curve may at times be edited to amend it in accordance with the particulars' parameters of the jaw in a particular teeth model. In the specific Example shown, the process is first performed for the upper jaw and then for the lower jaw, although it will be appreciated that this sequence may be altered, e.g. reversed, performed intermittently in the upper and lower jaws, etc.

In this specific embodiment, the orientation and position of the wire dictates the final result, i.e. final alignment of all slots in the bracket. In other words, in this specific embodiment a set of rules applied in the virtual treatment includes, at minimum, a requirement for vertical realignment of the slots, and hence of the teeth to which they are attached, so that all slots will arrive to the wire. The set of rules also dictate how to accomplish this result. Put differently, as a result of the virtual treatment, in the final orientation which will be accomplished in the resulting teeth model, the wire will remain at the same position and the teeth displaced such that the wire snaps into the slots of the bracket. This procedure is illustrated in FIG. 8., where the set of rules is dictated in blocks 81 and 82.

Figure 9:
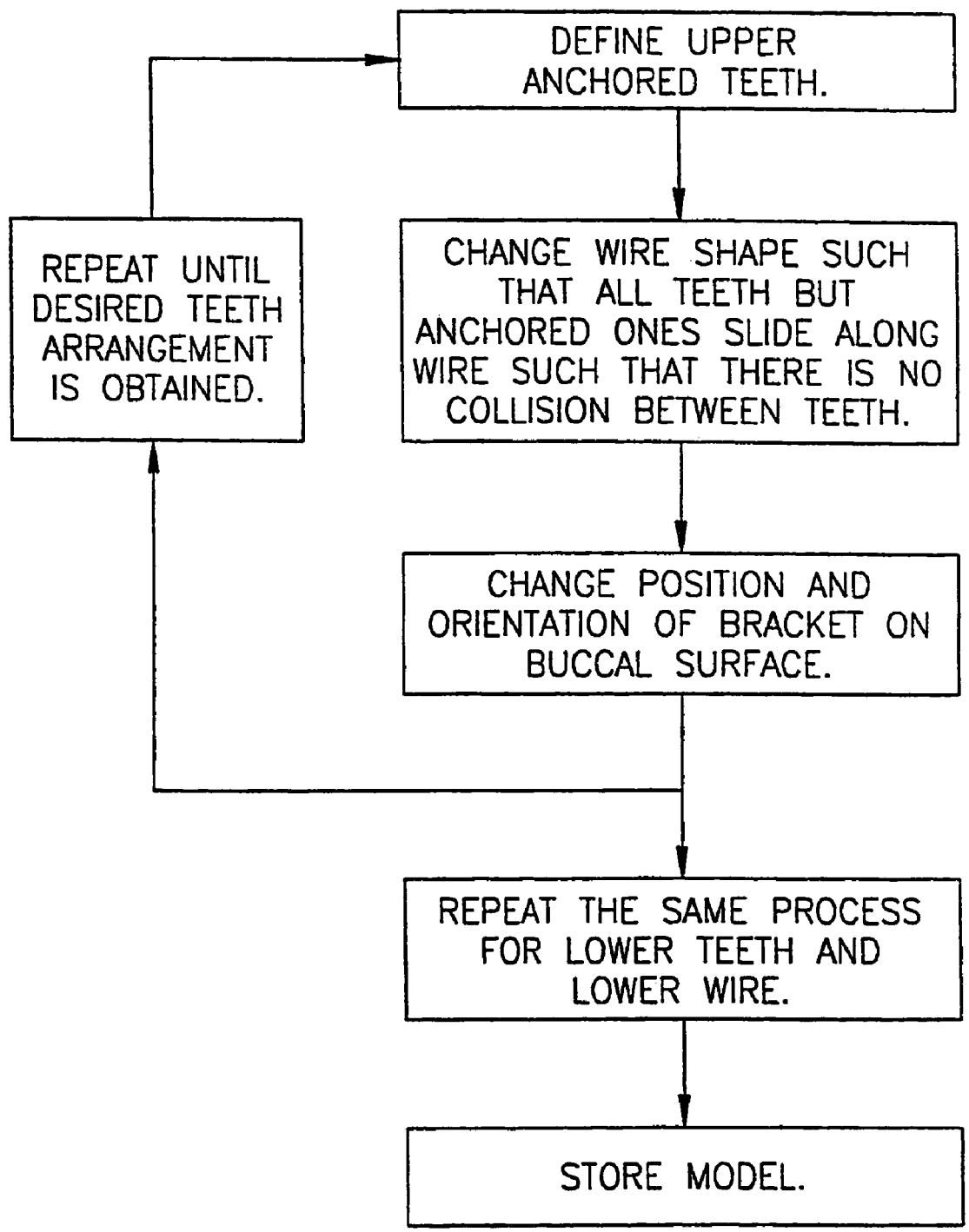
FIG. 9 is a block diagram illustrating the steps of horizontal movement of teeth in the case of crowdness, i.e. collision between teeth.

Another set of rules which can be applied in case of collision between the teeth, i.e. in case of crowdness. This is illustrated in FIG. 9 where the teeth are moved horizontally by sliding along the wire, to avoid such collision. The manner in which the virtual treatment is performed may allow also some user intervention. For example, the user can define some teeth which may have to remain stationary, and others which are allowed to move. Alternatively, the system may have a wider degree of freedom, to allow sideways movement of all teeth. As also illustrated in FIG. 9, it is possible in this process to provide the user with an additional degree of freedom, which involves changing the position and/or orientation of the bracket on the tooth surface.

Figure 10A:
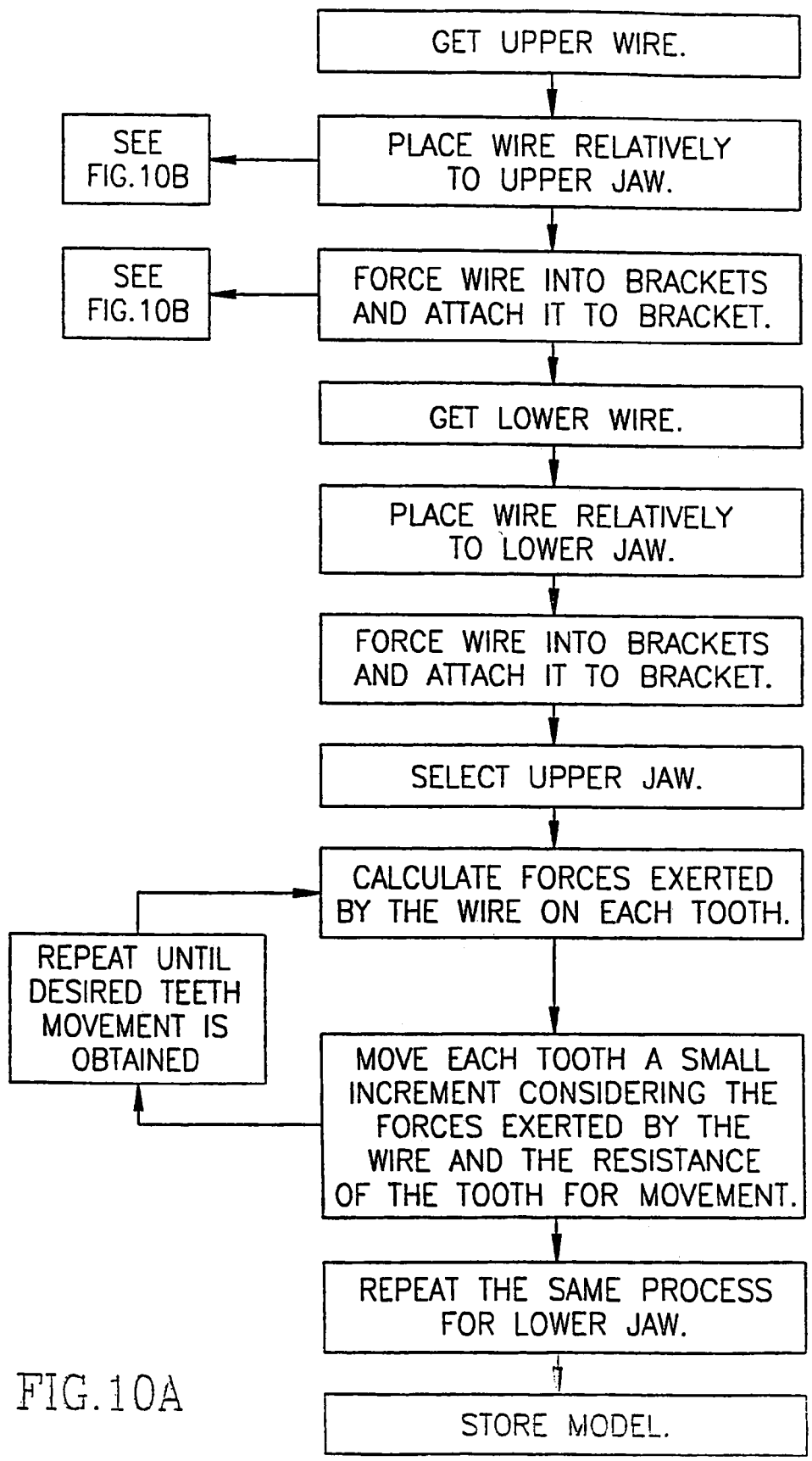
FIG. 10A is a block diagram illustrating the steps of matching wires to a jaw, in accordance with another embodiment of the invention, and movement of teeth as a result of virtual forces exerted by the wire or the teeth.
Figure 10B:
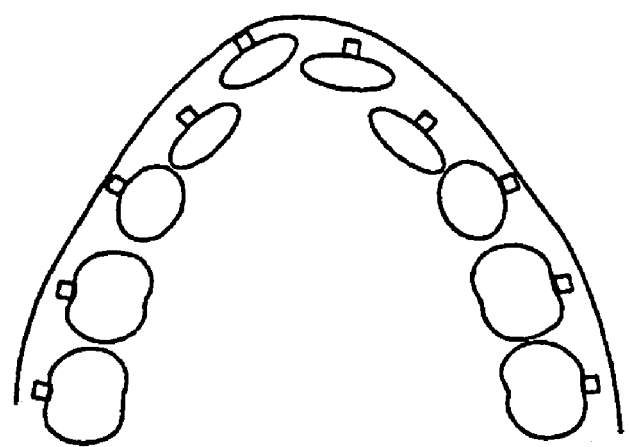
FIGS. 10B and 10C illustrate the manner in which the association between the wire and the teeth is viewed in two steps of the process of FIG. 10A.
Figure 10C:
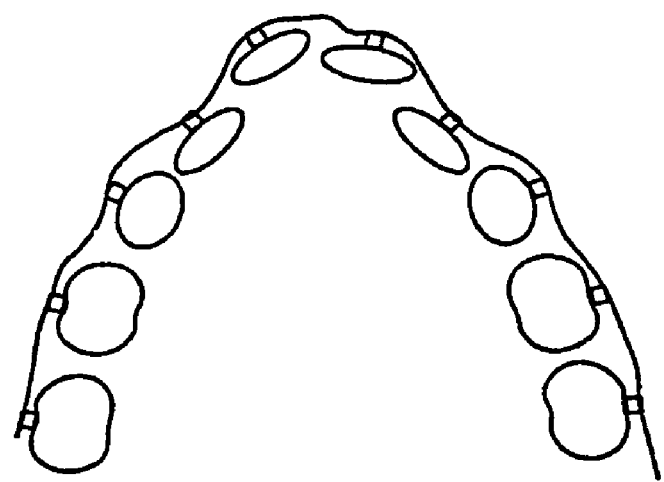

FIG. 10 illustrates another embodiment of teeth movement within the framework of a virtual treatment of the invention. As illustrated in FIG. 10A, wires are obtained, positioned in proximity of the jaw (illustrated graphically for the upper jaw in FIG. 10B), its shape edited so as to attach to the brackets on the teeth (illustrated graphically in FIG. 10C) and then the forces applied by the wire on the teeth are calculated and the final position of the teeth obtained can then be stored.

The present invention has been described with a certain degree of particularity but it should be understood that various modifications and alterations may be made without departing from the scope or spirit of the invention as defined by the following claims:

The invention claimed is:

1. A method for selecting orthodontic components for use in an orthodontic treatment of an individual, the method comprising:
   (i) in a computer:
      (a) selecting a virtual set of orthodontic components representing components that may be used in an orthodontic treatment,
      (b) providing a first virtual three-dimensional (3D) image of a 3D model of the individual's teeth comprising teeth of at least one jaw, the model being manipulable so as to allow its viewing from a desired direction,
      (c) associating the virtual set of components with the teeth in said virtual image in a manner resembling that in which such components are associated with teeth in an orthodontic treatment, to obtain a second image of said 3D model with said components associated therewith, and
      (d) using a set of rules, including at least one rule, defining the effect of said set of components on said teeth, computing the manner of movement of the teeth as a result of said effect, so as to obtain a third image comprising the teeth model following the virtual treatment; and
   (ii) generating a prescription for orthodontic treatment including specifying the type of components used based on the components of the virtual treatment.

2. A method according to claim 1, wherein step (i) is repeated a plurality of times, each time changing the manner in which at least one of steps (a), (c) or (d) is applied, until said third image shows a desired result of an orthodontic treatment and in step (ii) selecting a set of components resembling and having same properties as the virtual set that yielded said desired result.

3. A method according to claim 2, further comprising the step of outputting the manner of association of each orthodontic component in step (ii) with each corresponding tooth in said first image.

4. A method according to claim 1, wherein the set of orthodontic components comprises brackets, one for each tooth and one archwire for each jaw.

5. A method according to claim 1, wherein steps (c) and (d) are repeated a plurality of times.

6. A method according to claim 5, wherein in at least one of said repetitions of steps (c) and (d), a position and/or orientation of at least one said orthodontic components with respect to the tooth it is associated with is changed with respect to a position and/or orientation, respectively, previously held.

7. A method according to claim 5, wherein in at least one of said repetitions of steps (b) and (c), the type of orthodontic component associated with at least one tooth is changed with respect to the orthodontic component previously associated with said tooth.

8. A method according to claim 7, wherein in at least one of said repetitions of steps (b) and (c), a position and/or orientation of at least one said orthodontic components with respect to the tooth it is associated with is changed with respect to a position and/or orientation, respectively, previously held.

9. A method according to claim 1, comprising providing a user interface and wherein said selecting comprises using the user interface for selecting the virtual set of orthodontic components.

10. A method according to claim 1, wherein said associating comprises manually associating the selected brackets with the teeth of said first image.

11. A method according to claim 1, wherein predicting is used to design an orthodontic treatment.

12. A method according to claim 1, for predicting an outcome of an orthodontic treatment.

13. A method according to claim 1, wherein said first image is a virtual representation of a three-dimensional (3D) model of the individual's teeth at interim treatment stage and said third image is a virtual representation of an interim or a final treatment stage.

14. A method according to claim 1, wherein said set of rules is extracted from a dynamic learning database holding an adjustable rule base.

15. A method according to claim 14, wherein the adjustment of the database is based on characteristics of the individual undergoing the orthodontic treatment.

16. A method according to claim 1, comprising virtually extracting one or more teeth from the teeth model of said first image.

17. A method according to claim 16, wherein said set of rules include a rule that defines movement of teeth to occupy space previously occupied by an extracted tooth.

18. A method according to claim 16, wherein the virtually extracting is performed manually by a user.

19. A method according to claim 16, wherein the virtually extracting is performed automatically in case of teeth crowdness.

20. A method according to claim 1, comprising virtually adding a tooth to the model of said first image.

21. A method according to claim 20, wherein the added tooth represents one that has not yet grown.

22. A method according to claim 20, wherein the added tooth represents a crown that may be added or implanted in a real-life treatment.

23. A method according to claim 1, further comprising the step of outputting the manner of association of each orthodontic component in step (ii) with each corresponding tooth in said first image.

24. A method for selecting real-life orthodontic components for use in an orthodontic treatment of an individual, the method comprising:
  (i) in a computer:
    (a) selecting a virtual set of orthodontic components representing real-life orthodontic components that may be used in an orthodontic treatment, said virtual set of components simulating the components of said real-life set,
    (b) providing a first virtual three-dimensional (3D) image of a 3D model of the individual's teeth comprising teeth of at least one jaw, the model being manipulable so as to allow its viewing from a desired direction,
    (c) associating the virtual set of components with the teeth in said virtual image in a manner resembling that in which such components are associated with teeth in an orthodontic treatment, to obtain a second image of said 3D model with said components associated therewith, and
    (d) using a set of rules, including at least one rule, defining the effect of said set of components on said teeth, computing the manner of movement of the teeth as a result of said effect, so as to obtain a third image comprising the teeth model following the virtual treatment; and
  (ii) repeating step (i) a plurality of times until said substep (d) provides a desired result of the virtual treatment, wherein each time step (i) is repeated at least one of the following is changed:
    (A) in step (a) at least one said orthodontic components is changed for a different orthodontic component;
    (B) in step (b) said association of at least one said orthodontic component with respect to a tooth in said virtual image is changed with respect to the preceding association.

25. Method according to claim 24, wherein in step (A) said different orthodontic component comprises an orthodontic component previously used on a different tooth.

26. Method according to claim 24, wherein in step (A) said different orthodontic component comprises a new orthodontic component not previously comprised in said set of orthodontic components.

27. Method according to claim 24, wherein in step (B) said change in association comprises a change in at least one of a position and orientation of the orthodontic component with respect to the tooth.

28. A method according to claim 24, further comprising the step of outputting the manner of association of each orthodontic component at the end of step (ii) with each corresponding tooth in said first image.

* * * * *